US006746409B2

(12) United States Patent
Keirsbilck et al.

(10) Patent No.: US 6,746,409 B2
(45) Date of Patent: Jun. 8, 2004

(54) TECHNIQUE FOR DIAGNOSING ATTENTION DEFICIT HYPERACTIVITY DISORDER USING COMPLIMENTARY TESTS

(75) Inventors: Richard S. Keirsbilck, Rochester, NY (US); Richard N. Blazey, Penfield, NY (US); Peter A. Parks, Topeka, KS (US); David L. Patton, Webster, NY (US); Paige Miller, Rochester, NY (US)

(73) Assignee: The McLean Hospital Corporation, Belmont, MA (US)

( * ) Notice: Subject to any disclaimer, the term of this patent is extended or adjusted under 35 U.S.C. 154(b) by 236 days.

(21) Appl. No.: 10/076,261

(22) Filed: Feb. 14, 2002

(65) Prior Publication Data

US 2003/0158496 A1 Aug. 21, 2003

(51) Int. Cl.[7] .................................................. A61B 5/00
(52) U.S. Cl. ........................ 600/549; 600/300; 128/898
(58) Field of Search ............................... 600/26–28, 300, 600/301, 481, 500, 509, 544, 546, 549; 128/897, 898

(56) References Cited

U.S. PATENT DOCUMENTS

| | | | |
|---|---|---|---|
| 5,377,100 A | | 12/1994 | Pope et al. |
| 5,725,472 A | * | 3/1998 | Weathers ..................... 600/21 |
| 5,913,310 A | | 6/1999 | Brown |
| 5,918,603 A | | 7/1999 | Brown |
| 5,940,801 A | | 8/1999 | Brown |
| 5,947,908 A | * | 9/1999 | Morris ........................ 600/484 |
| 6,053,739 A | | 4/2000 | Stewart et al. |
| 6,097,980 A | | 8/2000 | Monastra et al. |
| 6,117,075 A | | 9/2000 | Barnea |
| 6,325,763 B1 | * | 12/2001 | Pfeiffer et al. .............. 600/549 |
| 6,394,963 B1 | * | 5/2002 | Blazey et al. ................ 600/549 |
| 6,565,518 B2 | * | 5/2003 | Blazey et al. ................ 600/549 |

OTHER PUBLICATIONS

Martin H. Teicher et al., Nature Magazine, Apr. 2000, vol. 6, No. 4, pp 470–473, Functional deficits in basal ganglia of children with attention–deficit/hyperactivity disorder shown with functional magnetic resonance imaging relaxometry.

Dr. Albert Rizzo et al., Human Factors and Cognitive/Perceptual Information Processing, "A Virtual Reality Environment for the Assessment of Attention Deficit Disorders in Children" Jul. 1999.

Joel F. Lubar, University of Tennessee, Biofeedback and Self–Regulation, vol. 16, No. 3, 1991, "Disclosure on the Development of EEG Diagnostics and Biofeedback for Attention–Deficit/Hyperactivity Disorders".

* cited by examiner

Primary Examiner—Charles Marmor
(74) Attorney, Agent, or Firm—Clark & Elbing LLP

(57) ABSTRACT

A method of determining threshold values, subsequently used to determine whether an individual has Attention Deficit Hyperactivity Disorder (ADHD) comprising: providing a group of subjects, a segment of which is known to have ADHD and a segment is known to not have ADHD; and testing each subject in the group by: (a) sampling the peripheral skin temperature of left and right like extremities during a predetermined time interval when the subject is in a sensory deprived state to provide respective left and right sampled peripheral skin temperature data; (b) processing the sampled peripheral skin temperature data, including filtering, differentiation, and conversion to the frequency domain to derive spectral signatures having magnitude values; and (c) final processing of spectral signatures for all of the subjects of the group to determine threshold values which are complimentarily effective for determining whether or not an individual has ADHD when tested by the testing method.

38 Claims, 9 Drawing Sheets

| | |
|---|---|
| Sample Rate (Hz): | 32.000000 |
| Stopband Freq (Hz): | 0.010000 |
| Passband Ripple (dB): | 12.000000 |
| Stopband Atten (dB): | 72.000000 |
| Cutoff Freq (Hz): | 0.020000 |
| Filter Order: | 32 |

Fig. 7

TECHNIQUE FOR DIAGNOSING ATTENTION DEFICIT HYPERACTIVITY DISORDER USING COMPLIMENTARY TESTS

FIELD OF THE INVENTION

This invention relates in general to a technique for diagnosing Attention Deficit Hyperactivity Disorder (ADHD) and more particularly to a technique for measuring and objectively analyzing an individual's peripheral temperature variability to determine values indicative of ADHD.

BACKGROUND OF THE INVENTION

ADHD is the most common neurobehavioral disorder of childhood as well as among the most prevalent health conditions affecting school-aged children. Between 4% and 12% of school age children (several millions) are affected. $3 billion is spent annually on behalf of students with ADHD. Moreover, in the general population, 9.2% of males and 2.9% of females are found to have behavior consistent with ADHD. Upwards of 10 million adults may be affected.

ADHD is a difficult disorder to diagnose. The core symptoms of ADHD in children include inattention, hyperactivity, and impulsivity. ADHD children may experience significant functional problems, such as school difficulties, academic underachievement, poor relationships with family and peers, and low self-esteem. Adults with ADHD often have a history of losing jobs, impulsive actions, substance abuse, and broken marriages. ADHD often goes undiagnosed if not caught at an early age and affects many adults who may not be aware of the condition. ADHD has many look-alike causes (family situations, motivations) and co-morbid conditions (depression, anxiety, and learning disabilities) are common.

Diagnosis of ADHD currently involves a process of elimination using written and verbal assessment instruments. However, there is no one objective, independently validated test for ADHD. Various objective techniques have been proposed but have not yet attained widespread acceptance. These include:

1. The eye problem called convergence insufficiency was found to be three times more common in children with ADHD than in other children by University of California, San Diego researchers.
2. Infrared tracking to measure difficult-to-detect movements of children during attention tests combined with functional MRI imaging of the brain were used by psychiatrists at McLean Hospital in Belmont, Mass. to diagnose ADHD in a small group of children (*Nature Medicine*, Vol. 6, No. 4, April 2000, Pages 470–473).
3. Techniques based on EEG biofeedback for the diagnoses and treatment of ADHD are described by Lubar (*Biofeedback and Self-Regulation*, Vol. 16, No. 3, 1991, Pages 201–225).
4. U.S. Pat. No. 6,097,980, issued Aug. 1, 2000, inventor Monastra et al, discloses a quantitative electroencephalographic process assessing ADHD.
5. U.S. Pat. No. 5,913,310, issued Jun. 22, 1999, inventor Brown, discloses a video game for the diagnosis and treatment of ADHD.
6. U.S. Pat. No. 5,918,603, issued Jul. 6, 1999, inventor Brown, discloses a video game for the diagnosis and treatment of ADHD.
7. U.S. Pat. No. 5,940,801, issued Aug. 17, 1999, inventor Brown, discloses a microprocessor such as a video game for the diagnosis and treatment of ADHD.
8. U.S. Pat. No. 5,377,100, issued Dec. 27, 1994, inventors Pope et al., discloses a method of using a video game coupled with brain wave detection to treat patients with ADHD.
9. Dr. Albert Rizzo of the Integrated Media Systems Center of the University of Southern California has used Virtual Reality techniques for the detection and treatment of ADHD.
10. U.S. Pat. No. 6,053,739, inventors Stewart et al., discloses a method of using a visual display, colored visual word targets and colored visual response targets to administer an attention performance test.

For Further Reference:

U.S. Pat. No. 5,377,100, issued Dec. 27, 1994, inventors Patton et al., discloses a system for managing the psychological state of an individual using images.

U.S. Pat. No. 6,117,075 inventor Barnea discloses a method of measuring the depth of anesthesia by detecting the suppression of peripheral temperature variability.

There are several clinical biofeedback and physiologic monitoring systems (e.g. Multi Trace, Bio Integrator). These systems are used by professional clinicians. Although skin temperature spectral characteristics have been shown to indicate stress-related changes of peripheral vasomotor activity in normal subjects, there has been no disclosure of use of variations in skin-temperature response to assist in diagnosing ADHD. (See: Biofeedback and Self-Regulation, Vol. 20, No. 4, 1995).

As stated above, the primary method for diagnosing ADHD is the use of a bank of written and verbal assessment instruments. These are designed to assess the individual for behavioral indicators of criteria established by American Medical Association (AMA) as described in the Diagnostic and Statistics manual (DSM-W). Psychiatrists, psychologists, the school psychologist or other licensed practitioner administer these assessment instruments. In some cases those individuals who meet DSM-IV criteria for ADHD diagnosis are prescribed a drug such as Ritalin. Behavioral observations of the patient while on Ritalin are conducted to assess the impact of prescribed medication.

There is thus a need for a simple, inexpensive, reliable, and objective technique for the diagnosis of ADHD.

SUMMARY OF THE INVENTION

According to the present invention, there is provided a solution to the problems and fulfillment of the needs discussed above.

According to a feature of the present invention, there is provided a method for determining two threshold values, which are subsequently used to determine whether an individual has Attention Deficit Hyperactivity Disorder (ADHD) comprising: providing a group of subjects, a segment of which is known to have ADHD and a segment of which is known to be normal and not have ADHD; testing the group by: (a) sampling the peripheral skin temperatures of left and right like extremities of each of said subjects, during a predetermined time interval when said subjects are in a sensory deprived state to provide respective left and right sampled peripheral skin temperature data; (b) a first processing of at least one of said left and right sampled peripheral skin temperature data with a Fast Fourier Transform (FFT) to derive a first spectral signature having magnitude values; (c) a second processing of both left and right sampled peripheral skin temperature data to derive temporally correlated differential data; (d) the second processing further filtering said differential data with a high pass filter to produce filtered data with near d.c. components removed; (e) the second processing finally applying an FFT to said filtered differential data to derive a second spectral signature having magnitude values; and (f) final processing of the first and second spectral signatures for all of the subjects of the group to determine two threshold values which are complimentarily effective for determining whether or not an individual has ADHD when tested by said testing procedure.

ADVANTAGEOUS EFFECT OF THE INVENTION

The invention has the following advantages.

1. A technique for objectively diagnosing ADHD is provided which is simple, inexpensive, and reliable.

BRIEF DESCRIPTION OF THE DRAWINGS

FIG. 7 is a table of the parameter values selected for the filter in accordance with the second processing of the present invention.

DETAILED DESCRIPTION OF THE INVENTION

According to the present invention, it has been found that signatures of ADHD are hidden in fluctuation of the temperature of the skin as measured at the extremities such as at the fingertips. It is well known in the art that as a person's stress level increases the blood vessels in the body constrict, as is evidenced by the fact that a person's blood pressure increases as their level of stress increases. As the blood vessels in the body contract, blood flow is restricted. This is most evident in the extremities such as the fingers, because the blood vessels in the extremities are small and furthest from the heart. A direct result of decreased blood flow to the blood vessels in the extremities is a decrease in the peripheral temperature of the extremities. Conversely, as a person's stress level decreases and one relaxes, the blood vessels also relax and dilate causing blood flow to increase. As the blood flow to the vessels in the extremities increases, the peripheral temperature of the extremities increases. When a subject with ADHD is subjected to sensory deprivation such as being made to look at a blank screen or an obscured image, the lack of stimulation increases and their level of anxiety and their stress level increases. As their stress level increases, their blood vessels constrict and the peripheral temperature of their extremities decreases. Biofeedback practitioners have long used measurement of hand temperature to help subjects manage their physiology by controlling blood flow to the extremities. The literature reports that reduced blood flow to the brain is frequently found in patients with ADHD.

Figure 1:
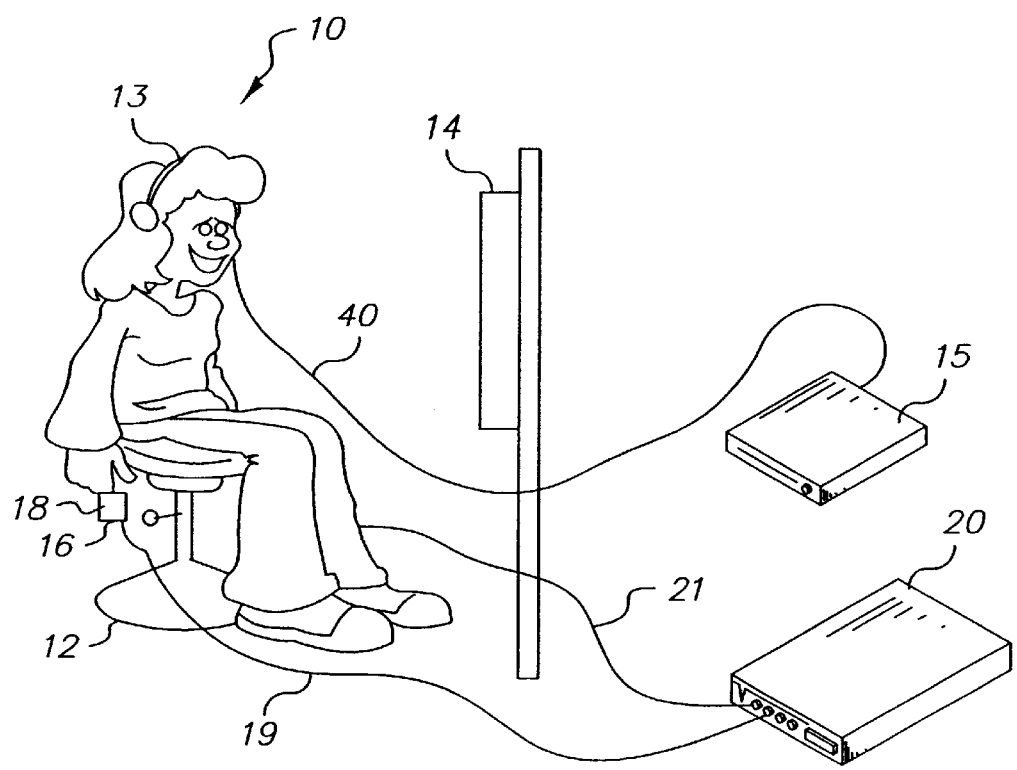
FIG. 1 is a diagrammatic view illustrating an embodiment of the present invention.

In the embodiment of the present invention shown in FIG. 1, a subject 10 is sitting on a chair 12 watching a screen 14 to minimize visual stimulus. Since said visual stimulus may be in the subject's peripheral vision, the screen 14 illustrated in FIG. 1 may be larger, for example a blank wall or corner of a room. The subject 10 is at rest in an inactive state. The subject 10 is shown wearing a set of headphones 13 connected via a wire 40 to a sound generating device 15 for producing white noise. The headphones 13 may be used to reduce or eliminate audio stimulus from the environment during the test. The method described in this embodiment of the present invention places the subject in sensory deprived surroundings. Other means for providing sensory deprivation are to have the subject wear a pair of translucent glasses, goggles or eye mask not shown. The glasses or goggles block any visual stimulus to the subject 10. These devices may be internally illuminated for uniformity and to further minimize the propensity to self-stimulate with mental images, which is easier to do with a dark 'slate' before one's eyes. For the same reason, the subject is instructed to not close their eyes, except to blink. In this embodiment, a sensor 18 measures the temperature of a fingertip 16 of subject 10. The temperature readings are supplied to module 20 via a wire 19. The temperature sensor for the opposite hand is not shown but is connected via wire 21 to module 20. In another embodiment not shown, the temperature can be taken from more than one location on each hand to increase the number of samples per session. The sensor glove disclosed in U.S. Pat. No. 6,589,171, may also be preferably used. Peripheral temperature may alternatively be sampled at the subject's feet or ears.

Figure 2:
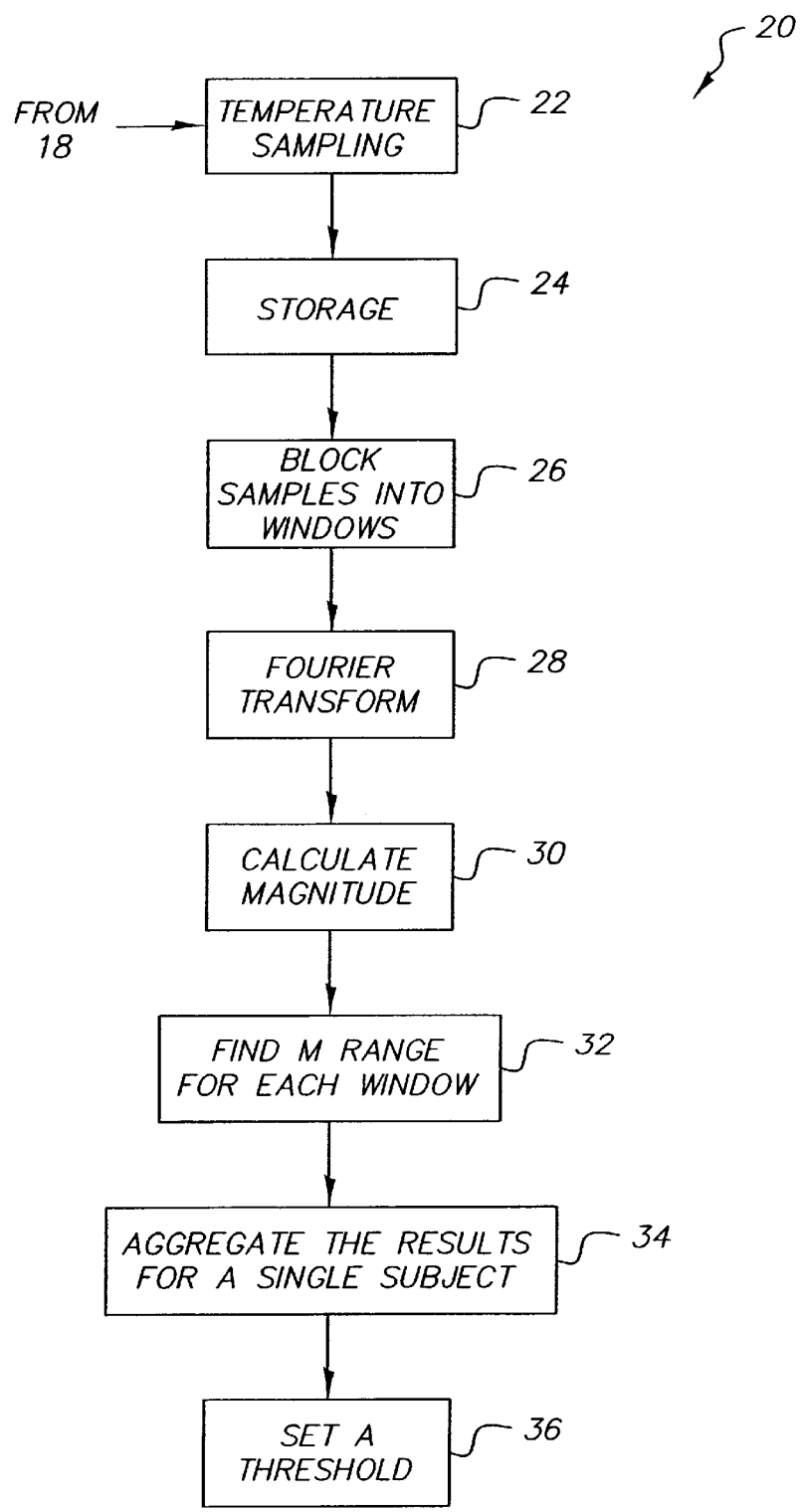
FIG. 2 is a block diagram of the acquisition and the first processing according to the present invention.

In FIG. 1, the fingertip temperatures are first recorded during an interval when the subject 10 has been asked to sit quietly for a period of about ten minutes. In FIG. 2, the said temperatures are sampled 22 at a time interval that provides 32 samples per second per sensor, creating at least two sets, left and right, of n temperature data, which are stored in storage 24.

First Processing

In the preferred embodiment of the present invention, a first processing is next carried out on these data. As shown in FIG. 2, module 20 includes window blocking 26, Fourier transform 28, Magnitude calculation 30, Mrange calculation 32, Aggregation step 34, and Thresholding step 36. In block 26, the n samples are divided into groups of m samples, each group corresponding to a given time window of width $\Delta t$ (~32–64 sec) equally spaced in time (~50 sec) across the entire baseline data collection time of 600 seconds. The data from each window is then passed through a Fast Fourier Transform (FFT) algorithm producing $2^{m-1}$ data points spaced equally in frequency space. The values are complex numbers having form $$FFT(f_m) = A(f_m) + B(f_m)i$$

where i is the $\sqrt{-1}$. The Phase $\Phi(f_m)$ is then found from the equation $$\Phi_l(f_m) = \mathrm{Tan}^{-1}\left(\frac{B(f_m)}{A(f_m)}\right) \qquad (1.0)$$

and the Magnitude $M(f_m)$ from $$M_l(f_m) = \sqrt{B(f_m)^{2+A(f_m)^2}} \tag{1.1}$$

Figure 3:
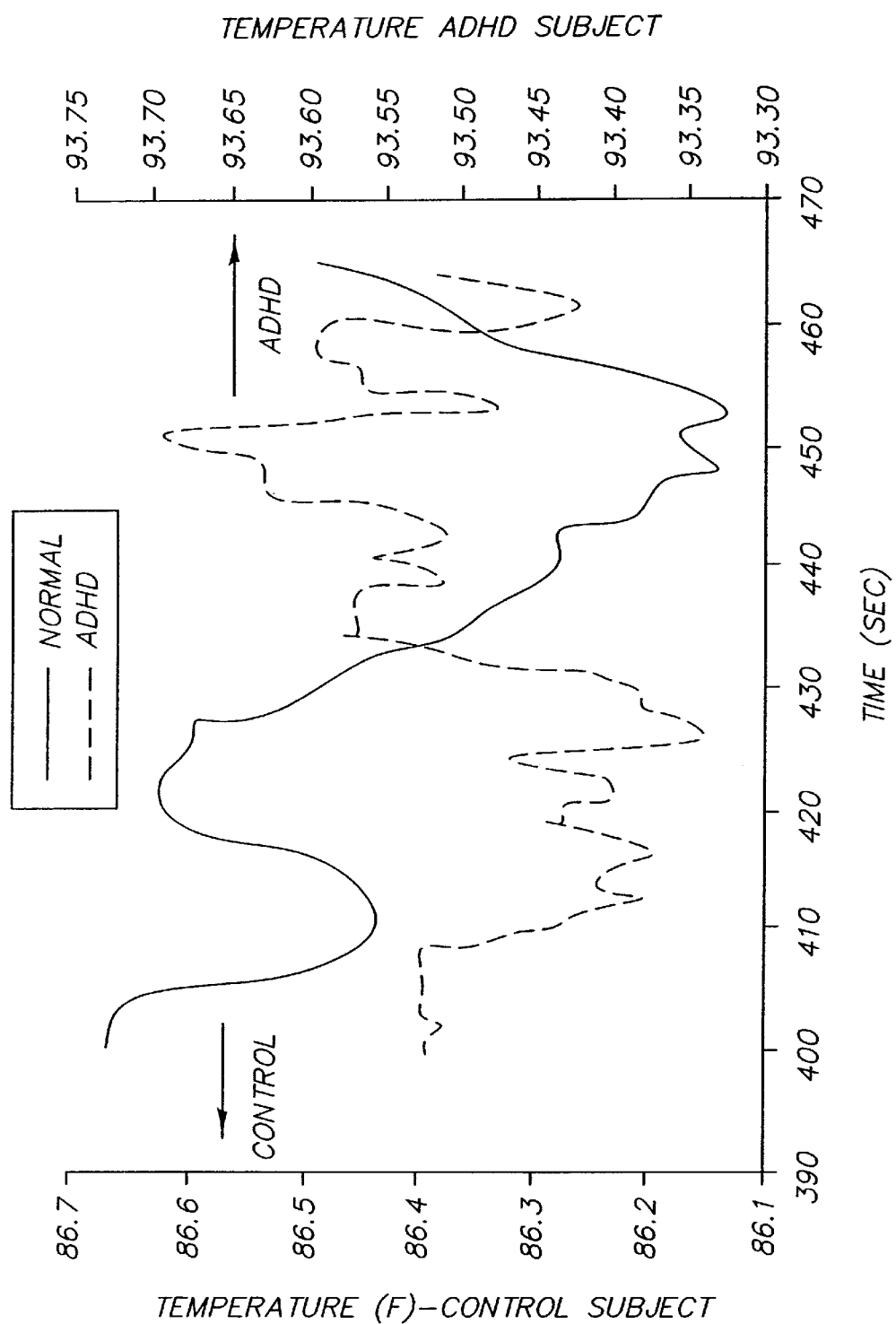
FIGS. 3, 4A and 4B are graphical views useful in explaining the first processing of the present invention.

In the equations 1.0 and 1.1 the subscript l refers to the fact that a separate signal is extracted for each hand so the subscript is l for data extracted from the left-hand data and r for data from the right hand. FIG. 3 graphically illustrates the temperature signal during one window for a normal subject and a person diagnosed with ADHD.

Figure 4A:
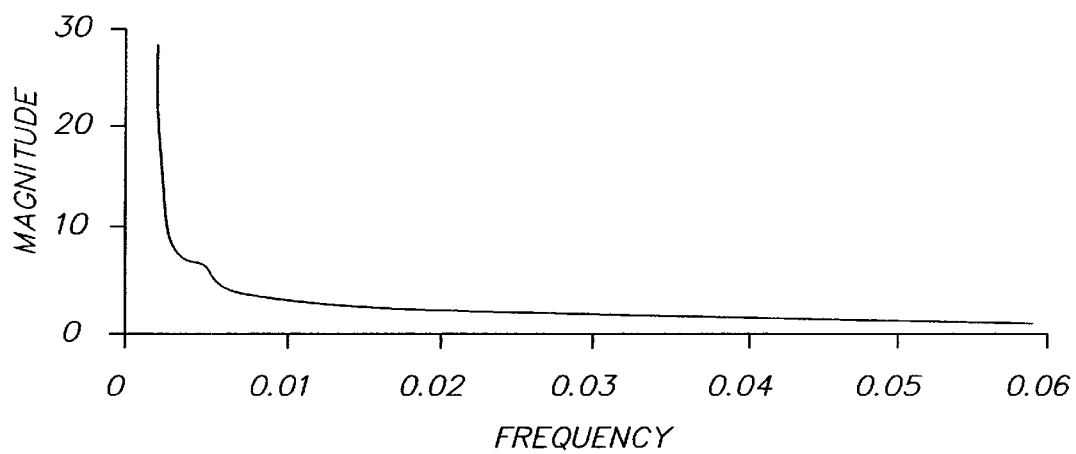
Figure 4B:
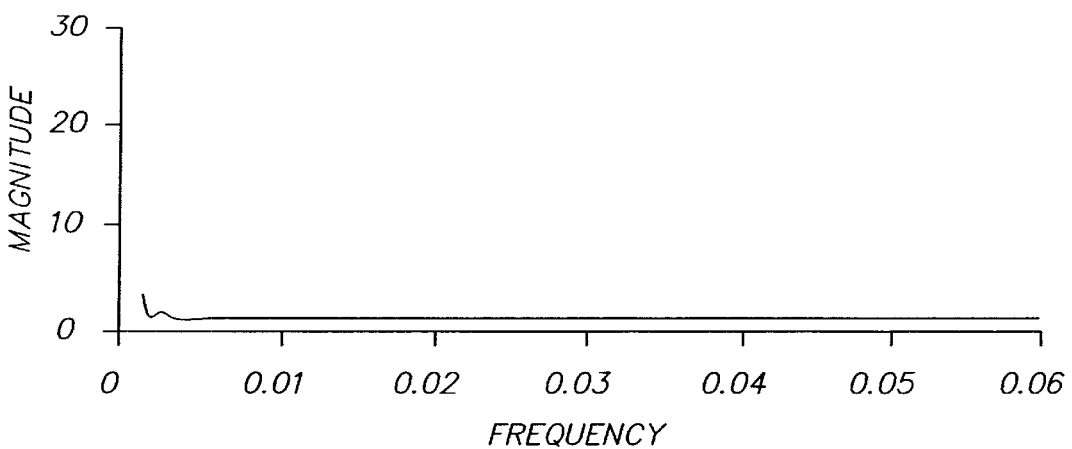

FIGS. 4A and 4B graphically illustrate the magnitude transform for the data corresponding with a subject with ADHD and normal subject. This spectral signature undergoes dramatic changes essentially changing from a hyperbolic curve to a flat response.

Referring again to FIG. 2.

Raw Data

The raw data $T_{k,l}(t)$ is the temperature taken from hand l at a fingertip 16 as shown in FIG. 1, during the 10-minute session. The sessions were taken over a period of weeks. Some subjects had as few as 2 sessions and some as many as 5 sessions. k is used to represent the session.

Windows

Referring to FIG. 2, the data for each session were divided into a series of windows (step 26) prior to performing the Fourier Transform operation 28. Call the window width w. In this analysis, the window width was 64 seconds and there were 10 windows spaced at 50-second intervals (the windows overlap) across the 600 second baseline spanning the range of 100–500 sec, other values of w can be used. The window number in a session is referred to with the letter j. For each window a FFT algorithm calculates the Fourier Transform F(f). The Magnitude and Phase of this transform are defined as given above.

In step 32 the range of magnitude variation during a window is calculated using equation (1.2) below where $f_{max}$ and $f_{min}$ are the frequencies where the Magnitude is the greatest and the least respectively (note the dc component at frequency zero is excluded).

$$M_{range} = [M(f_{max}) - M(f_{min})] \tag{1.2}$$

In a further embodiment of this method, other statistics from a Fourier Transform, calculated from the quantities denoted above as $A(f_m)$, $B(f_m)$, $\Phi(f_m)$, and $M(f_m)$ can be used. In addition to using Fourier Transforms, this further embodiment can use statistics derived from a Wavelet transform of the data or other filtering of the data (as in Strang, G. and Nguyen, T. (1996), *Wavelets and Filter Banks*, Wellesley-Cambridge Press, Wellesley, Mass.).

Aggregation of Samples

Samples are aggregated in step 34. There are 10 samples from each hand from each session. The first step is to choose an aggregation statistic which can be the mean, median, variance, or other statistic, which is an aggregate of the computed $M_{Range}$ values in each window for each session and each hand. Other statistics that can be used for aggregation include the standard deviation, range, interquartile distance, skewness, kurtosis, Winsorized mean and variance, and robust estimates of mean and variance. Equations below are given for aggregating the mean and the variance. The mean magnitude range for the left hand of session k is found from equation 2.0. where z is the number of windows in the session.

$$<M_{k,l}> = \frac{\sum_{j=1}^{z}[M(f_{max})_j - M(f_{min})_j]}{z} \tag{2.0}$$

And the corresponding variance is:

$$<Var_{k,l}> = \frac{\sum_{j=1}^{z}\{[M(f_{max})_{j,i} - M(f_{min})_{j,i}] - <M_{k,l}>\}^2}{z-1} \tag{2.1}$$

Combining these session means and variances over both hands and all the sessions s that a subject attended gives an aggregated mean $\mu$ and aggregated variance $var_i$.

$$\mu = \frac{\sum_{k=1}^{s}\sum_{l=1}^{2}<M_{k,l}>}{2s} \tag{2.2}$$

$$<var> = \frac{\sum_{k=1}^{s}\sum_{l=1}^{2}var_{k,l}}{2s} \tag{2.3}$$

Other embodiments of this aggregation step of the first processing include using the data from only one hand—either the left hand, the right hand, or the dominant hand (and if the subject is ambidextrous, the dominant hand would be defined as the average of both hands). In addition, these embodiments may not require averaging of several sessions, but selecting only one session for use or using a weighted combination of each session's results.

Thus, the totality of these embodiments of the first processing include methods that involve any and all combinations of: statistics derived from Fourier or Wavelet transformations or other filtering, plus any one of many possible aggregation statistics, plus using data from only one hand or the dominant hand or the average of both hands, plus using either all sessions or a subset of the sessions or a weighted combination of each session's results.

Diagnostic Indicator

In block 36 of FIG. 2, a diagnostic indicator is determined by setting a threshold level θ for the aggregation statistic in step 34. When the subject's measured aggregate statistic is less than the threshold θ, the test indicates the subject has ADHD. When the subject's measured aggregate statistic is greater than the threshold θ the test indicates the subject does not have ADHD. A single threshold may be used for all subjects or the threshold may be set differently for different groups such as gender or age.

The method of obtaining the threshold θ is now described. It is similar to a method in the statistical literature called "discriminant analysis". In fact, one could use discriminant analysis for this data; however this method was devised because it can be enhanced and used for purposes discriminant analysis cannot handle. This enhancement will be described later.

Figure 5:
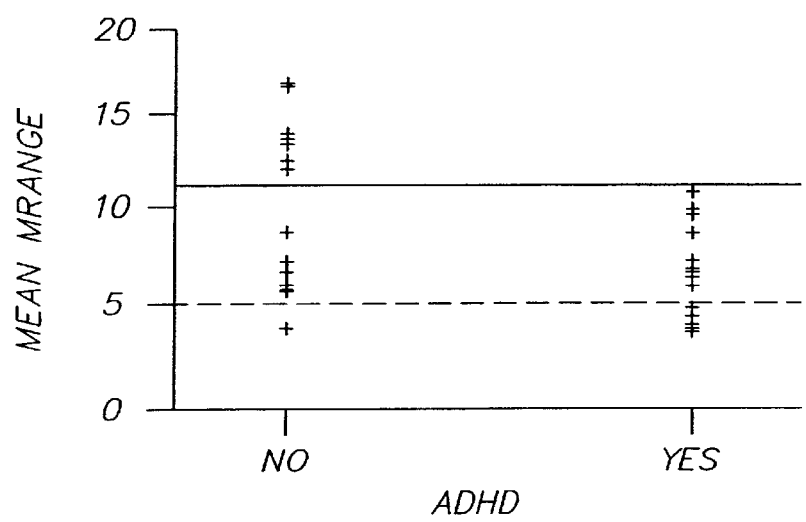
FIG. 5 is a diagram of an example of finding the proper threshold θ to separate ADHD subjects from non-ADHD subjects with the first processing of the present invention.

To find the value of θ that gives the highest percentage of correct diagnoses, a simple example must first be illustrated. In this example, there are 32 aggregation statistics, one for each subject in the study. Next thresholds θ=11.5 and θ=5 were considered. The 32 aggregation statistics are shown in FIG. 5, along with threshold θ=11.5 as the solid line and θ=5 as the dashed line. A different percent of correct diagnoses results when θ=11.5 is used compared to θ=5. Naturally, there are an infinite number of potential values for θ, and a procedure to pick the one that gives the highest percent of correct diagnoses is needed.

Thus, the following procedure was used: Twenty-five equally spaced values, spanning the range of the 32 aggregation statistics, were found. At each of these 25 values, the percent p of correctly diagnosed subjects was computed. A spline is fitted through this data, so that p is now estimated as a smooth function of θ. Then, the maximum value of this smooth function is found, and θ is set to be where the percent of correct diagnoses is maximized. Since this is often an interpolation, the value of the spline function at θ is not used, but instead is recomputed to percent of correct diagnoses at θ.

An enhanced method that works in situations where discriminant analysis does not work calls for replacing the percent of correct diagnoses in the above procedure with a weighted percent of false positive and false negative diagnoses, and then to minimize this weighted percent. This method allows the flexibility to choose the relative importance of false positive and false negatives, and to have this used in determining θ. One way to set the relative importance is to use the cost of a false negative diagnosis.

Virtually every analysis method tried produced correct diagnoses at a rate that is statistically above chance results at the $\alpha=0.05$ level, and many methods produced statistically significant results at the $\alpha=0.01$ level (see Table 1 through Table 8). This indicates that the diagnosis method proposed, using windowed Fourier transforms of hand temperatures, has found a real effect. The diagnoses obtained are significantly better than one would obtain using random chance.

For example, comparing the case where the variance was used on all data with one threshold for everyone, we see the method produces 68.8% correct diagnoses. If the variance is used with gender thresholds, the percent correct increases to 84.4%. Using different thresholds by gender improves the diagnoses when using all data, see Table 1. This is consistent with statements by Raymond, K. B. (1997). *Dissertation Abstracts International*: Section A: Humanities and Social Sciences, 57 (12-A) 5052, and also Katz, L., Goldstein, G., Geckle, M. (1998). Journal of Attention Disorders. 2(4), 239–47, who state that females with ADHD are underdiagnosed. This suggests that a different standard of diagnosis is necessary for females. Age based thresholds improve the percent correct by 3% (see Table 1). Any of the methods of separating thresholds by gender or age or neither, produce diagnoses that are statistically better than chance.

Another result shown in tables, reveals that removing noises (as described below) produce the highest percent correct diagnosis. This is consistent with the fact, that the data removed was contaminated and less likely to demonstrate the effect of interest. Further, note that without using gender or age thresholds after removing noises, the variance produces correct diagnoses 84.6% of the time. Using gender or age thresholds after removing noises, or using the mean or median, did not improve the results.

Listed below are the types of noise:

Self Diversion
  Children divert themselves by moving, using mental exercises or external tools such as gum or suckers.
External Stimulation
  Noises, Room Temperature, Parents in Room, etc.
Technical Problems
  Loose sensors, missing sensors, pauses, computer failures.
Sleep problems
  Child falls asleep during the session.

Medication Problems
  Child's medication is still active during session or child is on long acting drug.

For this first processing portion of the present invention, other analysis methods were tried and found to be less successful, though these methods were significantly better than chance. For example, applying a Butterworth filter to the raw temperature data as suggested by Shusterman, V. and Barnea, O. (1995). *Biofeedback and Self-Regulation*, 20(4), 357–365 did not produce improved results. Nor did separating the data by session (Table 7) or by hand (Table 8). The highest accuracy is obtained by averaging sessions and averaging two hands for tests. The benefit of using both sessions and both hands is that reduction of variability occurs, enabling more reliable diagnoses. A well-known statistical principle paraphrased is that the variability of the average of multiple sessions or two hands is less than the variability of one session or one hand. Nor did removing the first two time periods (Tables 3, 4 and 6) improve the percent of correct diagnoses.

The percent of false positive and false negative diagnoses was examined. Using the mean statistic and one threshold for all subjects, a result of 25% false positive diagnoses and 0% false negative diagnoses was achieved. Using separate thresholds by gender and the variance statistic produced a result of 9.4% false positive diagnoses, and 6.3% false negative diagnoses.

The test method was applied to 50% ADHD subjects and 50% non-ADHD subjects; however, if it was applied only to symptomatics (a subset of the population in which most have ADHD), it is shown below that the method test actually will produce higher accuracy. The actual rate of false diagnoses depends on the assumed percent of true ADHD subjects in the population of symptomatics to be tested.

Let p be the proportion of subjects in the study who actually have ADHD. Let $f_+$ be the proportion of false positive diagnoses of those subjects who do not have ADUD. Let $f_-$ be the proportion of false negative diagnoses of those subjects who do have ADHD. Then the proportion c of correct diagnoses is:

$$c=1-(f_-p-f_+(1-p))$$

The derivative of c is:

$$\frac{\partial c}{\partial p}=f_+ - f_-$$

The derivative is positive whenever $f_+$ is greater than $f_-$. Thus, increasing the value of p will increase the proportion c of correct diagnoses.

Note that the illustrative tables in the Appendix correspond to analysis methods of the first processing, as just described. For the second processing of the present invention next described, no corresponding references are provided in the Appendix.

Second Processing

In the preferred embodiment of the present invention, a second processing of the data allows the assessment of the bi-modality of the spectral energy of peripheral temperature variability where, for example, with ADHD subjects, the just described first processing determines a decrease of spectral energy below around 0.005 Hz. and the second processing next described determines an increase in bilaterally differential spectral energy around 0.03 Hz. The opposite bi-modality should be seen with non-ADHD subjects.

Figure 6:
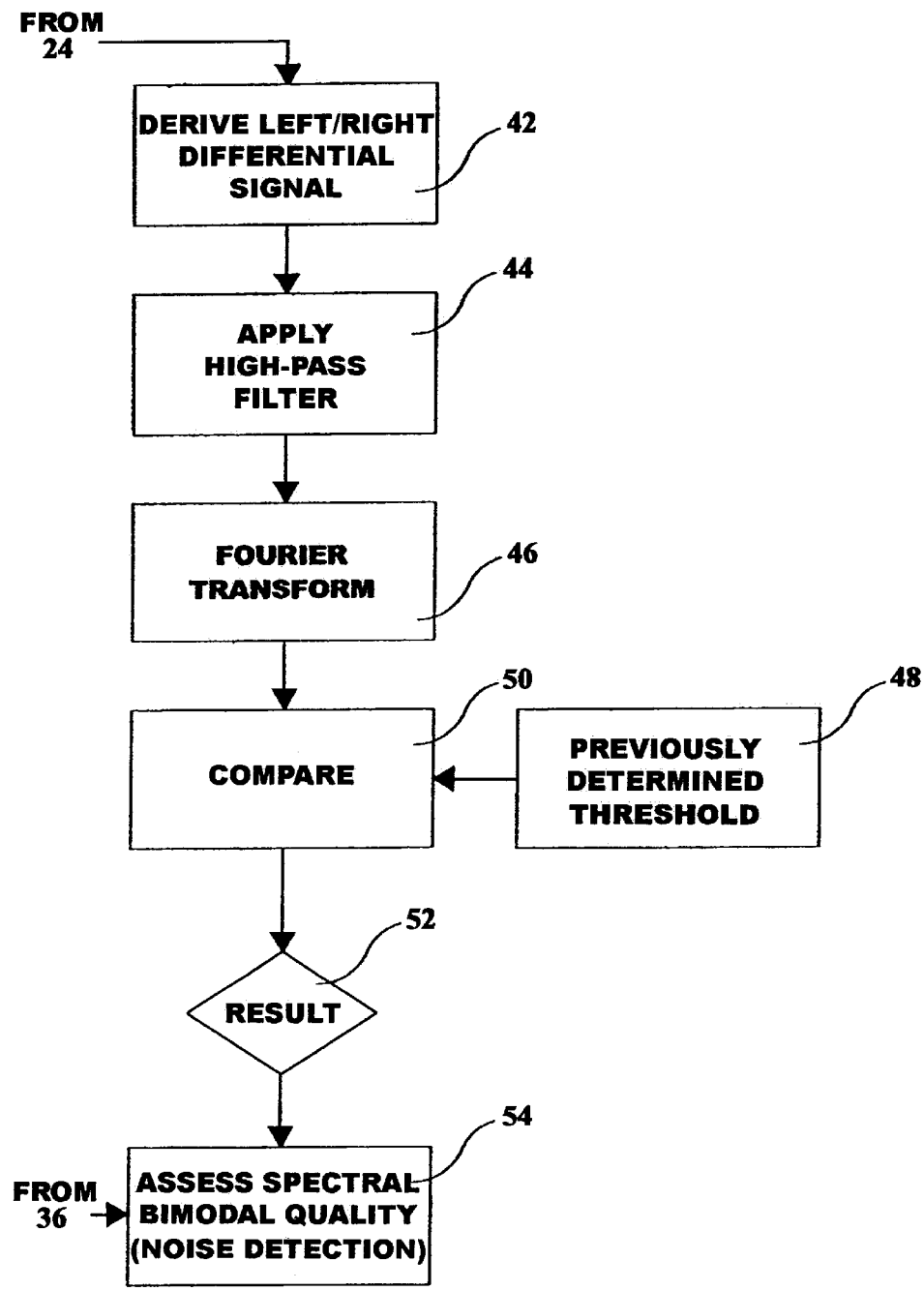
FIG. 6 is a block diagram of the second processing of the present invention.

Referring to FIG. 6, using the same sampled data from data storage 24 of FIG. 2, the first step in the second processing is to subtract each data value of one hand from the temporal companion data of the other hand, producing a differential value 42 for each sample period. Next, a Butterworth High-pass Infinite Impulse Response Filter 44 is applied to the differential data, producing a roll-off characteristic, increasingly attenuating towards frequency zero. Removing the near-dc components in this way allows for greater discrimination of the areas in the frequency domain of interest, empirically determined to center around approximately 0.03 Hz., with the described filtering.

Figure 8:
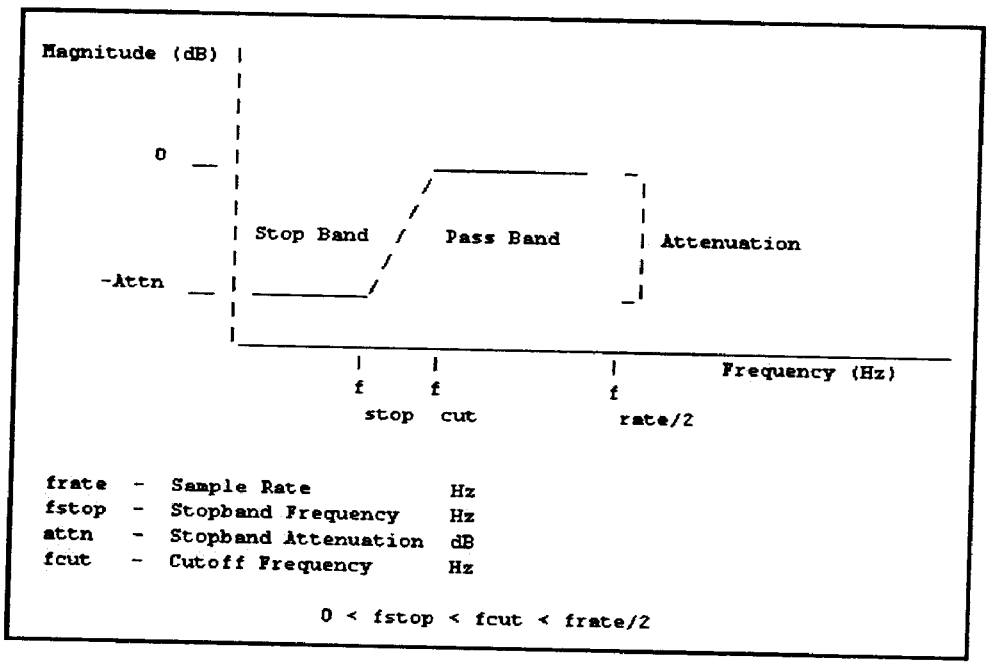
FIG. 8 is a graph of the filter parameters in accordance with the second processing of the present invention.
Figure 9:
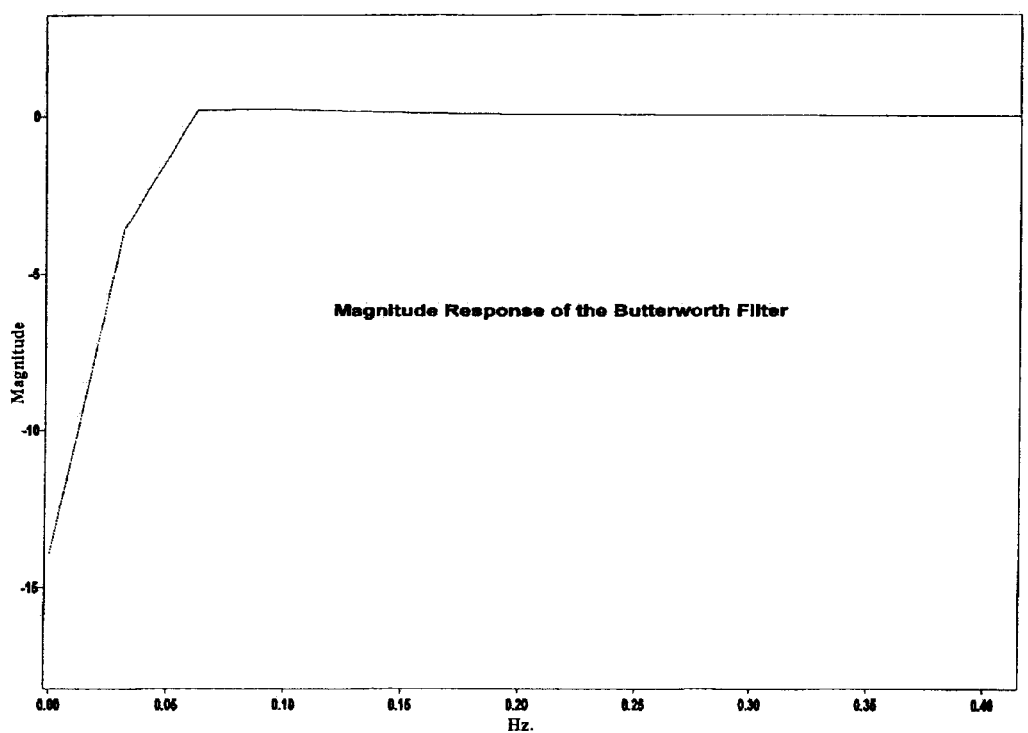
FIG. 9 is a plot of the spectral response of the filter of FIGS. 7 and 8.

As there may be differences in software to perform this transform, the application used is identified here as the DaDisp™ application by DSP Development Corporation. FIG. 7 is a table of the parameter values selected for the Butterworth Highpass IIR Filter 44. FIG. 8 is a graph of the Butterworth Highpass IIR Filter 44 parameters. FIG. 9 is a plot of the spectral response for the Butterworth Highpass IIR Filter 44 of FIGS. 7 and 8.

Figure 10:
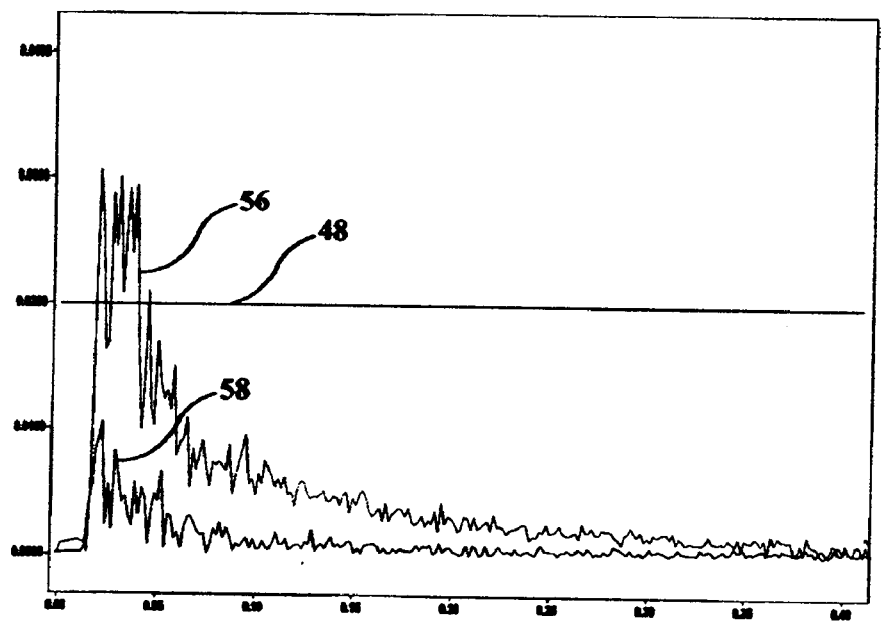
FIG. 10 is a sample of the second processing resultant spectral signature plots from two sessions, showing differing response.

The resultant high-passed differential data are then passed through a Fast Fourier Transform (also by DaDisp™) 46, producing a second spectral signature. A single magnitude threshold 48 is then applied 50. This magnitude threshold 48 is empirically determined in like manner to the first processing method, and was determined by a small sampling to be around magnitude 0.02 for the Filter 44 and Fast Fourier Transform 46 described. FIG. 10 illustrates sample resultant spectrum plots, wherein the threshold 48 segregates the ADHD subject 56 and non-ADHD subject 58.

Thusly, similar to the analysis method of the first processing, the just described second processing provides a means for detecting ADHD, that is, the magnitude of a final spectral signature. But with two differences: firstly, the portion of the spectrum of interest is centered around 0.03 Hz., and secondly, when the magnitude of the spectral signature is less than the threshold, the test indicates the subject does not have ADHD. When it is greater than the threshold, the test indicates the subject has ADHD.

It is therefore concluded here, considering the aforesaid determination, that very slow peripheral temperature variability is not simply suppressed in ADHD positive subjects, but rather, moves upward in frequency, and becomes markedly bilaterally differential in nature. The mechanism for this ADHD manifestation is thought to be the suppression of slower, common control of the left and right peripheral temperatures by the autonomic nervous system (sympathetic and/or parasympathetic), resulting in the control of temperature at said periphery being more localized and therefore more independent of each other.

Multiplicity of Tests

As herein before stated, a well known statistical principle is that the variability of the average of multiple tests is less than the variability of one test. Therefore, an advantage of effective, additional, concurrent testing, e.g., the combination of different first and second processing of the same session data, is increased accuracy.

Noise Detection

A key advantage of the method of the present invention that combines the first processing and the just described second processing is the ability to distinguish external noise from true physiological function. External noise will manifest as increased spectral content, which can occur anywhere in the spectrum, including within the regions of interest. It may be anywhere from broadband to very frequency-specific. Such noise is usually difficult to discern unless the specific frequency or bandwidth is known, which is not the case with such measurements.

The present invention provides a means for noise detection due to the nature of vasomotor activity. Peripheral temperatures are ultimately controlled in all cases, thereby producing the same total spectral energy on average. The present invention provides complimentary tests of this feature of physiology: that if the magnitude of energy is less in one spectral region, the case in the first processing with ADHD subjects, the magnitude of energy is greater in the other spectral region, the case in the second processing with the same said ADHD subjects. The matched opposites of these results indicates that the subject does not have ADHD. This bi-modal spectral characteristic will not be seen with noise since it can only be additive. Noise in the data is thereby identifiable. This is accomplished at the bi-modal quality assessment 54 of FIG. 6, which complimentarily compares the result of block 36 of FIG. 2 to result 52 of FIG. 6.

Note that this does not mean that the noise can be removed; the data is invalidated. Possible courses of action include excising a portion of the data, re-testing and/or the removal of the source of noise at the testing site.

According to the present invention then, the now described first and second processing result in the following possible test outcomes:

1) a non-ADHD diagnosis, 2) an ADHD diagnosis, and 3) there is noise in the data.

The invention has been described in detail with particular reference to certain preferred embodiments thereof, but it will be understood that further study could indicate refinements and optimizations, and that such variations and modifications can be effected within the spirit and scope of the invention.

APPENDIX

The following is a list of tables in the Appendix that show the percent of subjects correctly diagnosed by different analysis methods, or by using different portions of the data, or by a combination of analysis methods and different portions of the data (note that in all the following cases, sessions whose subjects had medication problems have been removed):

Table 1: All remaining data used

Table 2: Windows with technical problems (sensor falling off or pause button pushed) eliminated Table 3: First two time windows removed Table 4: Same as Table 2, but first two time windows are removed Table 5: Sessions where there were serious self-diversion problems were removed.

Table 6: Same as 5, but first two time periods were also removed.

Table 7: Same as 1, one threshold for all subjects, but data from only session 1, or only session 2 or both sessions were used.

Table 8: Same as 1, one threshold for all subjects, but data from left hand; or right hand; or dominant hand used.

TABLE 1

Percent of Correct Diagnoses
Subjects with medication problems removed (2822 & 2813 Session 1)
Both Hands/Both Sessions, N = 32
95% Significance is >65.6% correct, 99% Significance is >71.9% correct
Data used: All Data

| | Statistic Used: | | |
|---|---|---|---|
| Thresholds used | Mean % Correct Diagnoses | Median % Correct Diagnoses | Variance % Correct Diagnoses |
| One Threshold for Everyone | 75.00 | 68.75 | 68.75 |
| Age Thresholds | 78.13 | 71.88 | 71.88 |
| Gender Thresholds | 81.25 | 68.75 | 84.38 |

TABLE 2

Percent of Correct Diagnoses
Subjects with medication problems removed (2822 & 2813 Session 1)
Both Hands/Both Sessions, N = 32
95% Significance is >65.6% correct, 99% Significance is >71.9% correct
Data used: Remove technical problems

| | Statistic Used: | | |
|---|---|---|---|
| Thresholds used | Mean % Correct Diagnoses | Median % Correct Diagnoses | Variance % Correct Diagnoses |
| One Threshold for Everyone | 68.75 | 68.75 | 68.75 |
| Age Thresholds | 75.00 | 75.00 | 75.00 |
| Gender Thresholds | 78.13 | 68.75 | 81.25 |

TABLE 3

Percent of Correct Diagnoses
Subjects with medication problems removed
Both Hands/Both Sessions, N = 32
95% Significance is >65.6% correct, 99% Significance is >71.9% correct
Data used: Remove 1st 2 time periods

| | Statistic Used: | | |
|---|---|---|---|
| Thresholds used | Mean % Correct Diagnoses | Median % Correct Diagnoses | Variance % Correct Diagnoses |
| One Threshold for Everyone | 68.75 | 65.63 | 65.63 |
| Age Thresholds | 71.88 | 68.75 | 65.63 |
| Gender Thresholds | 71.88 | 65.63 | 68.75 |

TABLE 4

Percent of Correct Diagnoses
Subjects with medication problems removed
Both Hands/Both Sessions, N = 32
95% Significance is >65.6% correct, 99% Significance is >71.9% correct
Data used: Remove technical problems and 1st 2 time periods

| | Statistic Used: | | |
|---|---|---|---|
| Thresholds used | Mean % Correct Diagnoses | Median % Correct Diagnoses | Variance % Correct Diagnoses |
| One Threshold for Everyone | 65.63 | 65.63 | 68.75 |
| Age Thresholds | 71.88 | 68.75 | 68.75 |
| Gender Thresholds | 68.75 | 65.63 | 71.88 |

TABLE 5

Percent of Correct Diagnoses
Subjects with medication problems removed (2822 & 2813 Session 1)
Both Hands/Both Sessions, N = 26
95% Significance is >65.4% correct, 99% Significance is >73.1% correct
Data used: Remove tech/external/self-diverted problems

| | Statistic Used: | | |
|---|---|---|---|
| Thresholds used | Mean % Correct Diagnoses | Median % Correct Diagnoses | Variance % Correct Diagnoses |
| One Threshold for Everyone | 76.92 | 73.08 | 84.62 |
| Age Thresholds | 84.62 | 76.92 | 84.62 |
| Gender Thresholds | 76.92 | 76.92 | 84.62 |

TABLE 6

Percent of Correct Diagnoses
Subjects with medication problems removed (2822 & 2813 Session 1)
Both Hands/Both Sessions, N = 32
95% Significance is >65.4% correct, 99% Significance is >73.1% correct
Data used: Remove tech/external/self-diverted problems and
1st 2 time periods

| | Statistic Used: | | |
|---|---|---|---|
| Thresholds used | Mean % Correct Diagnoses | Median % Correct Diagnoses | Variance % Correct Diagnoses |
| One Threshold for Everyone | 73.08 | 65.38 | 73.08 |
| Age Thresholds | 80.77 | 76.92 | 76.92 |
| Gender Thresholds | 69.23 | 73.08 | 76.92 |

TABLE 7

Percent of Correct Diagnoses by Session
Subjects with medication problems removed (2822 & 2813 Session 1)
Data used: All Data

| | Statistic Used: | | |
|---|---|---|---|
| Session used | Mean % Correct Diagnoses | Median % Correct Diagnoses | Variance % Correct Diagnoses |
| Session 1 | 68.75 | 68.75 | 71.88 |
| Session 2 | 71.88 | 65.63 | 68.75 |
| Both Sessions | 75.00 | 68.75 | 68.75 |

TABLE 8

Percent of Correct Diagnoses by Hand
Subjects with medication problems removed (2822 & 2813 Session 1)
Data used: All Data

| | Statistic Used: | | |
|---|---|---|---|
| Hand Used | Mean % Correct Diagnoses | Median % Correct Diagnoses | Variance % Correct Diagnoses |
| Both Hands | 75.00 | 68.75 | 68.75 |
| Dominant Hand | 75.00 | 65.63 | 65.63 |
| Left Hand | 65.63 | 62.50 | 71.88 |
| Right Hand | 65.63 | 68.75 | 68.75 |

What is claimed is:

1. A method for determining two threshold values used to determine whether an individual has Attention Deficit Hyperactivity Disorder (ADHD) comprising:

providing a group of subjects a segment of which is known to have ADHD and a segment of which is known to be normal and not have ADHD;

testing the group by:
(a) sampling the peripheral skin temperature of left and right like extremities of each subject in the group during a predetermined time interval when they are in a sensory deprived state to provide respective left and right sampled peripheral skin temperature data;
(b) a first processing of at least one of said left and right sampled peripheral skin temperature data providing conversion to the frequency domain to derive a first spectral signature having magnitude values;
(c) a second processing of both left and right sampled peripheral skin temperature data to derive temporally correlated differential data;
(d) said second processing further filtering said differential data with a high pass filter to produce filtered differential data with near d.c. components removed;
(e) said second processing lastly providing conversion to the frequency domain of said filtered differential data to derive a second spectral signature having magnitude values; and
(f) a third processing of said first and second spectral signatures for all of the subjects of the group to determine respective first and second threshold values which are complimentarily effective for determining whether or not an individual has ADHD when tested by said testing method.

2. The method of claim 1 wherein said left and right extremities sampled are the pair of said subject's two hands or two feet.

3. The method of claim 2 wherein one or more digits of each of said pair are sampled during said sampling.

4. The method of claim 1 wherein said left and right extremities sampled are said subject's ears.

5. The method of claim 1 wherein said differential data is derived by subtracting one of said left and right sampled data from the other of said left and right sampled data.

6. The method of claim 1 wherein said high pass filter is a Butterworth Highpass Infinite Impulse Response Filter.

7. The method of claim 1 wherein said second spectral signature has a spectral response of interest which is centered around approximately 0.03 Hz.

8. The method of claim 1 wherein said third processing uses discriminant analysis to determine said first threshold value.

9. The method of claim 1 wherein said third processing uses descriminant analysis to determine said second threshold value.

10. The method of claim 1 wherein said third processing uses a selected percent of correct diagnoses to determine said first threshold value.

11. The method of claim 1 wherein said third processing uses a selected percent of correct diagnoses to determine said second threshold value.

12. The method of claim 1 wherein said third processing uses a selected weighted percent of false positive and/or false negative diagnoses to determine said first threshold value.

13. The method of claim 1 wherein said third processing uses a selected weighted percent of false positive and/or false negative diagnoses to determine said second threshold value.

14. The method of claim 1 wherein said group of subjects provided include individuals of both male and female gender in each segment; and wherein acceptable threshold values are determined for each of said genders.

15. The method of claim 1 wherein said group of subjects provided include individuals in at least two different age groups in each segment; and wherein acceptable threshold values are determined for each of said different age groups.

16. The method of claim 1 wherein during said testing, one or more of the following causes of noise are minimized: self diversion, ambient visual and auditory stimulation, technical problems, sleep problems, and medication problems.

17. The method of claim 1 including providing headphones adapted to be worn by said subjects during said predetermined time interval to block out ambient noise or to receive white noise to reduce or eliminate auditory stimulus from the ambient environment during said predetermined time interval.

18. The method of claim 17 including a source of white noise coupled to said headphones to provide white noise during said predetermined time interval.

19. The method of claim 1 including providing glasses or goggles adapted to be worn by the subject to block out or eliminate visual stimulus from the ambient environment during said predetermined time interval.

20. The method of claim 19 including presenting a uniformly illuminated visual field to said subjects during said predetermined time interval to minimize the human propensity to self-stimulate with mental imagery.

21. A method of determining whether an individual has Attention Deficit Hyperactivity Disorder, comprising:

testing the individual by:
(a) sampling the peripheral skin temperatures of left and right like extremities of the individual during a predetermined time interval when the individual is in a sensory deprived state to provide respective left and right sampled peripheral skin temperature data;
(b) a first processing of at least one of said left and right sampled peripheral skin temperature data providing conversion to the frequency domain to derive a first spectral signature having magnitude values;
(c) a second processing of both left and right sampled peripheral skin temperature data to derive temporally correlated differential data;
(d) said second processing further filtering said differential data with a high pass filter to produce filtered differential data with near d.c. components removed;
(e) said second processing lastly providing conversion to the frequency domain of said filtered differential data to derive a second spectral signature having magnitude values;
(f) a third processing of the said first spectral signature for the determination of the manifestation of ADHD by comparison to a predetermined first threshold value;
(g) a fourth processing of the said second spectral signature for the determination of the manifestation of ADHD by comparison to a predetermined second threshold value; wherein said predetermined first and second threshold values are determined by the method of claim 1; and
(h) a fifth processing wherein an assessment of the bi-modal quality of the results of the third and fourth processing is made, to provide a final determination of one of three possibilities:
(1) the thusly-tested individual has ADHD;
(2) the thusly-tested individual does not have ADHD; and
(3) there is noise in the data.

22. The method of claim 21 wherein said left and right extremities sampled are the pair of said individuals two hands or two feet.

23. The method of claim 22 wherein one or more digits of each of said pair are sampled during said sampling.

24. The method of claim 21 wherein said left and right extremities sampled are said individual's ears.

25. The method of claim 21 wherein said differential data is derived by subtracting one of said left and right sampled data from the other of said left and right sampled data.

26. The method of claim 21 wherein said high pass filter is a Butterworth Highpass Infinite Impulse Response Filter.

27. The method of claim 21 wherein said second spectral signature has a spectral response of interest which is centered around approximately 0.03 Hz.

28. The method of claim 21 wherein different threshold values are used for each of both genders.

29. The method of claim 21 wherein different threshold values are used for each of different age groups.

30. The method of claim 21 wherein during said testing, one or more of the following causes of noise are minimized: self diversion, ambient visual and auditory stimulation, technical problems, sleep problems, and medication problems.

31. The method of claim 21 including providing headphones adapted to be worn by the individual during said predetermined time interval to block out ambient noise or to receive white noise to reduce or eliminate auditory stimulus from the ambient environment during said predetermined time interval.

32. The method of claim 31 including providing a source of white noise coupled to said headphones to provide white noise during said predetermined time interval.

33. The method of claim 21 including providing glasses or goggles adapted to be worn by the individual to block out or eliminate visual stimulus from the ambient environment during said predetermined time interval.

34. The method of claim 33 including presenting a uniformly illuminated visual field to the individual during said predetermined time interval to minimize the human propensity to self-stimulate with mental imagery.

35. The method of claim 21 wherein said fifth processing assessment requires that both:
   (a) said first spectral signature has a magnitude less than said first threshold value, and
   (b) said second spectral signature has a magnitude greater than said second threshold value, in order for a diagnosis of ADHD to be made.

36. The method of claim 21 wherein said fifth processing assessment requires that both:
   (a) said first spectral signature has a magnitude greater than said first threshold value, and
   (b) said second spectral signature has a magnitude less than said second threshold value, in order for a diagnosis of non-ADHD to be made.

37. The method of claim 21 wherein said fifth processing assessment provides that obtaining only one of two requirements:
   (a) said first spectral signature has a magnitude less than said first threshold value, and
   (b) said second spectral signature has a magnitude greater than said second threshold value, determines the presence of noise in the data, thereby invalidating said data.

38. The method of claim 21 wherein said fifth processing assessment provides that obtaining only one of two requirements:
   (a) said first spectral signature has a magnitude greater than said first threshold value; and
   (b) said second spectral signature has a magnitude less than said second threshold value, determines the presence of noise in the data, thereby invalidating said data.

* * * * *

UNITED STATES PATENT AND TRADEMARK OFFICE
CERTIFICATE OF CORRECTION

PATENT NO. : 6,746,409 B2
APPLICATION NO. : 10/076261
DATED : June 8, 2004
INVENTOR(S) : Keirsbilck et al.

It is certified that error appears in the above-identified patent and that said Letters Patent is hereby corrected as shown below:

Column 1, Line 57, replace "et al" with --et al. --.

Column 2, Line 35, replace "DSM W" with --DSM IV--.

Column 5, Line 2ff., Equation 1.1, replace "$B(f_m)2+A(f_m)2$" with --$B(f_m)^2+A(f_m)^2$--.

Column 6, Line 10ff., Equation 2.1, replace "$(f_{max})_{j,\ i}$" with --$(f_{max})_{j,\ I}$--.

Column 7,
    Line 59, replace "suckers." with --suckers--; and
    Line 65, replace "failures." with --failures--; and
    Line 67, replace "session." with --session--.

Column 8, Line 38, replace "ADUD" with --ADHD--.

Column 10,
    Line 52, replace "used" with --used. --; and
    Line 54, replace "eliminated" with --eliminated. --; and
    Line 55, replace "removed" with --removed. --; and
    Line 57, replace "removed" with --removed. --.

Column 12, Line 63, after Table 8 insert:
-- PARTS LIST
10    subject
12    chair
13    headphones
14    screen
15    sound generating device
16    fingertip
18    sensor
19    wire
20    module
21    wire
22    temperature sampling circuit
24    data storage
26    window blocking
28    Fourier transform
30    Magnitude calculation
32    Mrange calculation
36    thresholding step
40    wire

UNITED STATES PATENT AND TRADEMARK OFFICE
CERTIFICATE OF CORRECTION

PATENT NO. : 6,746,409 B2
APPLICATION NO. : 10/076261
DATED : June 8, 2004
INVENTOR(S) : Keirsbilck et al.

It is certified that error appears in the above-identified patent and that said Letters Patent is hereby corrected as shown below:

Column 12, Line 63, after Table 8 insert: PARTS LIST (cont'd)
42   derivation block
44   filter block
46   Fourier transform block
48   magnitude threshold
50   comparison block
52   result
54   noise detection block
56   ADHD subject plot
58   non-ADHD subject plot--.

Column 13,
   Line 1, replace "subjects" with --subjects,--; and
   Line 49, replace "descriminant" with --discriminant--.

Column 14, Line 18, after "including, insert --providing--.

Column 15, Line 2, replace "individuals" with --individual's--.

Signed and Sealed this

Twenty-second Day of May, 2007

JON W. DUDAS
*Director of the United States Patent and Trademark Office*